US007255706B2

(12) United States Patent
Rosengart (10) Patent No.: US 7,255,706 B2
(45) Date of Patent: Aug. 14, 2007

(54) APPARATUS AND METHOD FOR CUTTING A HEART VALVE

(76) Inventor: Todd K. Rosengart, 1016 Brittany Rd., Highland Park, IL (US) 60035-3952

( * ) Notice: Subject to any disclaimer, the term of this patent is extended or adjusted under 35 U.S.C. 154(b) by 183 days.

(21) Appl. No.: 10/706,506

(22) Filed: Nov. 12, 2003

(65) Prior Publication Data

US 2004/0116951 A1   Jun. 17, 2004

Related U.S. Application Data

(60) Provisional application No. 60/426,078, filed on Nov. 13, 2002.

(51) Int. Cl.
*A61B 17/32* (2006.01)
(52) U.S. Cl. ...................... 606/170; 128/898
(58) Field of Classification Search ............... 128/898; 606/14; 623/2.11
See application file for complete search history.

(56) References Cited

U.S. PATENT DOCUMENTS

| 3,946,503 | A |   | 3/1976  | Buchan et al. ................ 35/9 |
| 5,295,958 | A | * | 3/1994  | Shturman ............. 604/103.07 |
| 5,352,240 | A |   | 10/1994 | Ross .......................... 623/2 |
| 5,370,685 | A | * | 12/1994 | Stevens ................... 623/2.11 |
| 5,443,446 | A |   | 8/1995  | Shturman .................... 604/49 |
| 5,480,424 | A |   | 1/1996  | Cox .............................. 623/2 |
| 5,545,214 | A | * | 8/1996  | Stevens ...................... 606/191 |
| 5,584,803 | A | * | 12/1996 | Stevens et al. ............ 604/6.16 |
| 5,688,261 | A |   | 11/1997 | Amirkhanian et al. ....... 606/17 |
| 5,722,970 | A |   | 3/1998  | Colvard ........................ 606/3 |
| 5,799,282 | A |   | 8/1998  | Rakshit et al. ................ 705/2 |
| 5,823,948 | A |   | 10/1998 | Ross, Jr. et al. ............ 600/300 |
| 5,984,959 | A |   | 11/1999 | Robertson et al. ............. 623/2 |
| 5,999,909 | A |   | 12/1999 | Rakshit et al. ................ 705/2 |
| 6,014,630 | A |   | 1/2000  | Jeacock et al. ................ 705/3 |
| 6,033,419 | A |   | 3/2000  | Hamblin, Jr. et al. ....... 606/184 |
| 6,149,440 | A |   | 11/2000 | Clark et al. ................. 434/322 |
| 6,171,112 | B1 |  | 1/2001  | Clark et al. ................. 434/322 |
| 6,203,553 | B1 |  | 3/2001  | Robertson et al. .......... 606/139 |
| 6,238,412 | B1 | * | 5/2001  | Dubrul et al. .............. 606/200 |
| 6,309,417 | B1 |  | 10/2001 | Spence et al. ............. 623/2.11 |
| 6,338,735 | B1 | * | 1/2002  | Stevens ...................... 606/159 |
| 6,413,274 | B1 |  | 7/2002  | Pedros ...................... 623/2.11 |
| 6,638,303 | B1 |  | 10/2003 | Campbell .................. 623/2.2 |
| 6,830,584 | B1 | * | 12/2004 | Seguin ...................... 623/2.11 |
| 6,896,690 | B1 | * | 5/2005  | Lambrecht et al. ......... 606/200 |
| 2001/0044591 | A1 | * | 11/2001 | Stevens et al. ............ 604/6.11 |
| 2002/0058995 | A1 | * | 5/2002  | Stevens ...................... 623/2.11 |
| 2004/0034380 | A1 | * | 2/2004  | Woolfson et al. ........... 606/170 |
| 2004/0210304 | A1 | * | 10/2004 | Seguin et al. ............. 623/2.11 |

FOREIGN PATENT DOCUMENTS

FR           2800984        5/2001
WO        WO 99/59482      11/1999

* cited by examiner

*Primary Examiner*—Henry M Johnson, III
(74) *Attorney, Agent, or Firm*—Kilyk & Bowersox, P.L.L.C.

(57) ABSTRACT

An apparatus for cutting and removing a tissue is described, which includes a rotational axle device, at least one non-mechanical cutting device radially disposed from the rotational axle device, at least one device capable of protecting the heart ventricle, and a first collapsible plate. Also described is a method for cutting a tissue, such as a heart valve using the apparatus of the present invention and temporary placing a device capable of protecting the heart ventricle until a percutaneous heart valve is placed.

33 Claims, 5 Drawing Sheets

APPARATUS AND METHOD FOR CUTTING A HEART VALVE

This application claims the benefit under 35 U.S.C. §119 (e) of prior U.S. Provisional Application No. 60/426,078 filed Nov. 13, 2002, which is incorporated in its entirety by reference herein.

BACKGROUND OF THE INVENTION

The surgical procedure for heart valve replacement typically involves removing a diseased heart valve and implanting an artificial heart valve device. Removal of the diseased heart valve generally involves cutting the valve from the heart to form an annulus in which the replacement valve is implanted. Conventional cutting processes for forming the heart valve annulus involve the use of scissor devices to cut the existing valve tissue from the heart. Frequently, the valve is extremely calcified and irregular in shape and thickness, thus to remove the valve in its entirety, exertion of considerable mechanical forces are required, which can cause cutting the valve in small pieces and releasing chunks of calcium or tissue.

This conventional use of scissors often produces imprecise cuts and leaves an irregular annulus in which the surgeon must then attach or suture the replacement valve. Because of the irregular annulus left by the use of scissors and other debriding instruments, the suturing process can be quite time-consuming. In particular, the surgeon must ensure that there are no openings around the replacement valve that would allow blood to flow from the heart chamber without passing through the replacement valve. More importantly, a considerable force cannot be used to remove a calcified valve when a device is placed and is manipulated percutaneously, as in through a transvascular catheter placed through a peripheral artery, such as the femoral artery.

Another apparatus that could be used to remove a diseased heart valve is an apparatus having an annulus cutter that is moved toward a backup plate in order to engage the tissue to be removed. The rotation of the annulus cutter by a surgeon would cut the tissue. The tissue is then captured by the cutting device and the backup plate. Such a device is described in International Publication No. WO 99/59482, which is incorporated in its entirety by reference herein. However, this procedure has several disadvantages. For example, the cut may still be imprecise and furthermore, parts of the cut tissue can inadvertently be dislodged from the capturing device. The dislodged tissue can cause an occlusion and embolism. More importantly, a large diameter cutting annulus could not be placed percutaneously through a small diameter peripheral artery, such as the femoral artery. In addition, it would be difficult and risky to transmit the considerable mechanical forces needed to cut a calcified valve through a percutaneously placed mechanical cutting device.

Accordingly, a need exists for a new improved method and apparatus for cutting living tissue, such as a heart valve.

SUMMARY OF THE PRESENT INVENTION

A feature of the present invention is to provide an apparatus for cutting and removing tissue with a precise cut in order to avoid leaving an irregular annulus.

Another feature of the present invention is to provide a rotational axle device to allow a user to make more precise cuts into tissue and to create an annulus.

A further feature of the present invention is to provide a non-mechanical cutting device that is capable of making precise cuts into tissue without a need for transmitting mechanical forces.

An additional feature of the present invention is to provide an apparatus for cutting a heart valve.

Also, a feature of the present invention is to provide a first collapsible plate and a second collapsible plate to obtain any loose or cut tissues in order to reduce the risk of an embolism.

A further feature of the present invention is to provide a first collapsible plate and a second collapsible plate having an adjustable diameter to allow the first and second collapsible plates to be introduced into the body through a relatively narrow diameter peripheral vessel, and then be expanded to a diameter approximately equivalent to that of one of the heart valves, such as the aortic valve.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention as embodied and broadly described herein, the present invention relates to a method for cutting a heart valve. The method provides for inserting a guide device into a vascular system of a patient, navigating the guide device to a predetermined location in the heart, advancing a first elongated instrument over the guide device and navigating the first elongated instrument to a predetermined location in the heart, advancing a second elongated instrument over the first elongated instrument and navigating the second elongated instrument to a predetermined location in the heart, and advancing a non-mechanical cutting device over the second elongated instrument to a predetermined position. Alternatively, the non-mechanical cutting device may be incorporated in (or be a part of) the second elongated instrument. Furthermore, the method provides for a distal end of the first elongated instrument or the second elongated instrument having a first collapsible plate to be on one side of the heart valve and extending the first elongated instrument or the second elongated instrument having a second collapsible plate through the heart valve, so that the distal end of the first elongated instrument or the second elongated instrument having the second collapsible plate is on the opposing side of the heart valve. The method also provides for expanding the first collapsible plate and the second collapsible plate.

The present invention further relates to a method for removing a damaged heart valve using a laser or other non-mechanical devices.

It is to be understood that both the foregoing general description and the following detailed description are exemplary and explanatory only and are intended to provide a further explanation of the present invention, as claimed.

The accompanying drawings, which are incorporated in and constitute a part of this application, illustrate various aspects of the present invention and, together with the description, serve to explain the principles of the present invention.

DETAILED DESCRIPTION OF THE PRESENT INVENTION

The present invention relates to an apparatus and a method for cutting and removing tissue (for example, living tissue) from a mammal. Preferably, the tissue that is being removed is a valve, and more preferably, the tissue that is being removed is a heart valve from a mammal, such as a human heart valve. In general, the apparatus of the present invention includes a rotational axle device, a first collapsible plate, and at least one non-mechanical cutting device. The present invention further relates to the method of removing a heart valve using the apparatus of the present invention.

Figure 1:
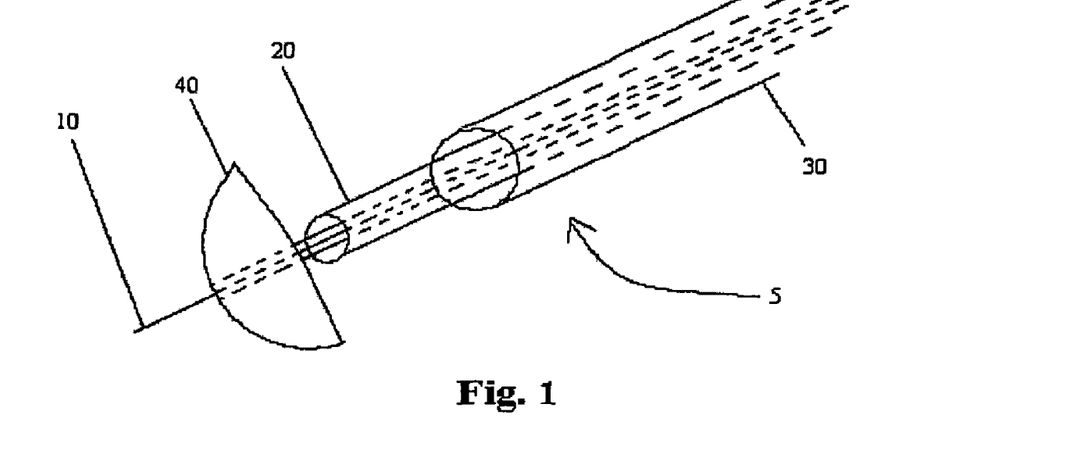
FIG. 1 is a schematic diagram showing a rotational axle device of the present invention, which includes a guide device, a first elongated instrument, a second elongated instrument, and a second collapsible plate.

The rotational axle device of the present invention can include any device that can be inserted into the vascular system of a patient, preferably into the aorta and/or the heart. Preferably, the rotational axle device is capable of acting as a rotational axle for devices that may be connected to or may be within an approximate distance of the rotational axle device. Preferably, the rotational axle device includes a guide device; a first elongated instrument having a proximal and a distal end; a second elongated instrument having a proximal and a distal end; and a second collapsible plate. In one example, as shown in FIG. 1, the rotational axle device 5 includes the guide device 10; the first elongated instrument 20; the second elongated instrument 30; and the second collapsible plate 40. The rotational axle device may also include at least one stabilizer (not shown) to place and maintain or fix the device in a predetermined location. The rotational axle device may optionally include at least one device capable of protecting the ventricle from reflux during diastole or from retrograde flow from an external pump source. Preferably, the device capable of protecting the ventricle is at least one inflatable balloon. The stabilizer may be or may include a retractable pin(s), a barb(s), a balloon(s), a hook(s), or any combination thereof, and may be placed/disposed at the distal end of the rotational axle device.

The guide device can be rigid or flexible. Preferably, the guide device is flexible. In the preferred embodiment, the guide device is an aortic guide device, and more preferably, the aortic guide device is an aortic guide wire. The reference to "aortic" for aortic guide device is to better explain the location of use of the guide device and the size and shape requirements that would preferably be used in view of its location of use. This will be true for the other terms preceding "aortic guide wire" and the like. The guide device is capable of following an artery, such as the femoral artery, to the aorta and/or at least one of the chambers in the heart. Preferably, the guide device includes at least one marker to allow the location of the guide device to be determined, for example, by a surgeon. Preferably, the marker is a radio-opaque marker. The guide device can be made from any non-toxic material. Preferably, the guide device is made from stainless steel wire. An example of a guide device 10 is shown in FIG. 1. Various guide devices are commercially available. In an alternative embodiment, the guide device may possess a hemostatic object, such as an inflatable balloon at its distal end. The balloon may be inflated once the valve is removed to prevent reflux of blood back into the ventricle. Once the native valve is removed, a new artificial or replacement valve may be inserted percutaneously over the guide device.

Figure 2:
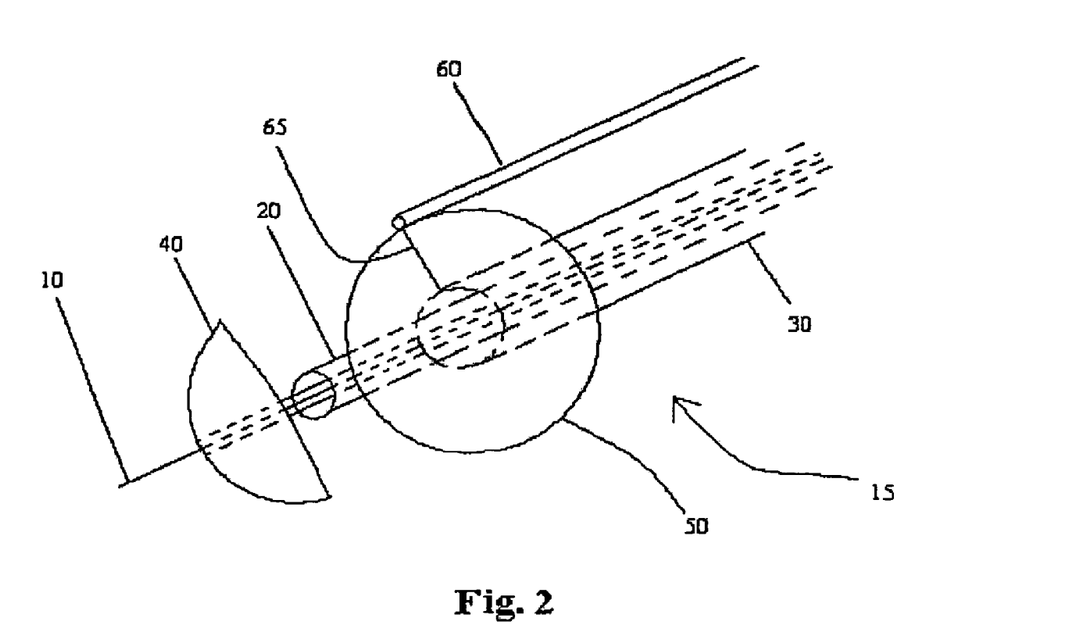
FIGS. 2 and 6 are schematic diagrams showing a first collapsible plate, a non-mechanical cutting device, a guide device, a first elongated instrument, a second elongated instrument, and a second collapsible plate of the present invention, where the non-mechanical cutting device is associated with/on the second elongated instrument as shown in FIG. 2 and the non-mechanical cutting device is associated with/on the first elongated instrument as shown in FIG. 6.

The first elongated instrument that is insertable into the vascular system of a patient is, preferably, a first catheter that is adapted to advance over the guide device. Preferably, the first elongated instrument is of a size and shape to be able to advance over the guide device from an artery (e.g., the femoral artery) to the aorta. More preferably, the first elongated instrument is of a size and shape to be able to advance through at least the damaged valve in the heart. Preferably, the diameter of the first elongated instrument is from about 3 mm or less to about 6 mm or more. The first elongated instrument may include at least one stabilizer to place and hold the instrument in a predetermined location. The first elongated instrument stabilizer may be or may include a retractable pin(s), a barb(s), a balloon(s), or any combinations thereof, and may be located at the distal end of the first elongated instrument within the heart ventricle, or may be located proximally in the aorta. An example of the first elongated instrument 20 is shown in FIGS. 1 and 2. Various types of elongated instruments are commercially available. The first elongated instrument can include a second collapsible plate, a first collapsible plate, a non-mechanical cutting device, or any combination thereof. Preferably, the first elongated instrument includes a second collapsible plate at its distal end.

The second elongated instrument that is insertable into the vascular system of a patient is, preferably, a second catheter that is adapted to advance over the first elongated instrument. Preferably, the second elongated instrument is of a size and shape to be able to advance over the first elongated instrument from an artery (e.g., the femoral artery) to the aorta. Preferably, the diameter of the second elongated instrument is from about 6 mm or less to about 10 mm or more. The second elongated instrument may include at least one stabilizer to place and hold the instrument in a predetermined location. The second elongated instrument stabilizer may be or may include a retractable pin(s), a barb(s), a balloon(s), or any combinations thereof, and may be located at the distal end of the second elongated instrument and be positioned within the heart ventricle, or may be located proximally in the aorta. Optionally, the second elongated instrument can be of a size and shape to be able to advance through at least the damaged valve in the heart. An example of the second elongated instrument is a second catheter that is commercially available. The second elongated instrument can include a first collapsible plate, a second collapsible plate, a non-mechanical cutting device, or any combination thereof. Preferably, the second elongated instrument includes a first collapsible plate and a non-mechanical cutting device. More preferably, the second elongated instrument includes a first collapsible plate.

The second collapsible plate can advance to a predetermined location from the peripheral artery by the first elongated instrument or by the second elongated instrument. Preferably, the second collapsible plate is advanced through the heart valve and is converted into its uncollapsed form approximate to the heart valve. Thus, in one example, in which the second collapsible plate is advanced into the aorta or into the heart, by the first elongated instrument, the diameter of the second collapsible plate, when in a collapsed form, is of a size to fit inside the first elongated instrument. In another example, in which the second collapsible plate is advanced into the aorta or into the heart by the second elongated instrument, the diameter of the second collapsible plate, when in a collapsed form, is of a size and shape to fit inside the second elongated instrument. Preferably, when the second collapsible plate is in a collapsed form, the second collapsible plate is from about 2 mm or less to about 10 mm or more in diameter. Moreover, when the second collapsible plate is in an expanded form, the second collapsible plate can have a diameter of from about 15 mm or less to about 30 mm or more. The expanded form of the second collapsible plate can be in any shape or form suitable to obtain a cut tissue and prevent any loss of tissue debris. Preferably, the second collapsible plate is conical in shape. FIG. 1 is an example that illustrates the relationship of the second collapsible plate 40 with respect to the first elongated instrument 20 and the second elongated instrument 30.

In one example, the second collapsible plate may be self-expandable. In this example, the natural configuration of the collapsible plate is in a form of its expanded configuration, such as a cone. The second collapsible plate can be maintained in its collapsed configuration by being constrained within the first or second elongated instrument. When the second collapsible plate is removed from the first or second elongated instrument, the second collapsible plate expands to its natural configuration. In another example, the second collapsible plate may be remotely expanded and/or retracted by struts or parachute cords. In this example, the struts or cords can pass through the inside of the first or second elongated instrument, and can be attached to the collapsible plate. The plate can be expanded or retracted by advancing or withdrawing the struts or cords, respectively.

The second collapsible plate can also include a filter (e.g., can be a membrane, screen, porous film, or other screening design) to allow blood flow through the second collapsible plate. Preferably, the pores are of a sufficient size to allow blood flow, but prevent any loose tissues/debris from escaping into the blood stream of a patient. Preferably, the pores are from about 50 μm to about 1 mm in diameter.

Optionally, the second collapsible plate can include at least one marker for determining its location in the vascular system. Preferably, the marker is a radio-opaque marker. Furthermore, a second collapsible plate may include at least one stabilizer to place and/or maintain the second collapsible plate in a predetermined location. The stabilizer may be or may include a retractable pin(s), a barb(s), a balloon(s), a hook(s) or any combination thereof that are able to stabilize/secure the second collapsible plate to the ventricular outflow tract proximal to the aortic valve. The stabilizer may be located anywhere on the second collapsible plate that would allow the stabilizer to stabilize and/or secure the second collapsible plate. Preferably, the stabilizer may be located at the edge of the second collapsible plate. Additionally, the stabilizer may be used to secure the second collapsible plate to the tissue to be removed and/or to the tissue after it has been cut. Preferably, a cut tissue is secured between a first collapsible plate and the second collapsible plate. Preferably, the second collapsible plate and the first collapsible plate are magnetized or adapted to possess opposite polarities to attract each other and to secure the cut tissue between the first collapsible plate and the second collapsible plate. Alternatively, the first collapsible plate and the second collapsible plate may oppose each other and secure the cut tissue there between by mechanical tension (pulling on the second collapsible plate while pushing on the first collapsible plate).

The second collapsible plate can be made from any material known in the art. Preferably, the second collapsible plate is made from a radio-opaque material and/or material impervious to the energy source used to cut the valve. More preferably, the second collapsible plate is made from a material through which laser light does not pass. Most preferably, the second collapsible plate is made from a deformable material, such as a plastic. Additionally, the second collapsible plate may include a sensor capable of detecting penetration of a specific wavelength (e.g., the wavelength of a laser), generated by the non-mechanical cutting device, which is penetrating through a tissue. Preferably, the sensor is capable of detecting transmural laser penetration. Such a sensor can be a photo-electric or other appropriate sensor known in the art.

The first collapsible plate can advance to a predetermined location from the peripheral artery by the first elongated instrument or the second elongated instrument. Preferably, the first collapsible plate is advanced to the aorta and is converted into its uncollapsed form (e.g. open form or expanded form) approximate to the heart valve. In one example, in which the first collapsible plate is advanced into the aorta by the first elongated instrument, the surface of the first collapsible plate, when in its uncollapsed (expanded) form, is of a size to cover/reach an area extending from an outer surface of the first elongated instrument to the inner surface of the second elongated instrument and/or the non-mechanical cutting device. In this example, the second elongated instrument is adapted to advance over the first elongated instrument, and can have a diameter of about or substantially equal to the diameter of a vessel (i.e., artery) at a location in which the valve or tissue is connected to the vessel (i.e., artery) or can have a smaller diameter. In this example, the diameter of the second elongated instrument is from about 10 mm or less to about 30 mm or more and the diameter of the first collapsible plate, when expanded, is from about 10 mm or less to about 30 mm or more. Alternatively, the first collapsible plate can be advanced into the aorta by the first elongated instrument and the surface of the first collapsible plate, when in its uncollapsed (expanded) form, is of a size to cover/reach an area extending from an outer surface of the first elongated instrument to the non-mechanical cutting device. Preferably, the first collapsible plate is advanced into the aorta by the second elongated instrument. Preferably, the surface of the first collapsible plate, when in its uncollapsed form, is of a sufficient size to cover an area extending from the outer surface of the second elongated instrument to the non-mechanical cutting device. Preferably, the non-mechanical cutting device is placed or disposed near the connecting point of a heart valve and the vessel (i.e., artery). When the diseased heart valve is inside the heart, then the non-mechanical cutting device is placed or disposed near the connecting point of a heart valve and the heart. In this example, the surface area of the first collapsible plate, when in its uncollapsed form, is from about 10 mm to about 30 mm in diameter. In another example, the first collapsible plate, when in its uncollapsed form, is of a size to cover the area from the surface of the second elongated instrument to about the inner surface of the vessel (i.e., artery).

When the first collapsible plate is in an expanded form, it can be in any shape or form capable of obtaining a cut tissue or tissue debris to prevent loss of tissue/debris. Preferably, the first collapsible plate is a diaphragm that prevents escape of tissue debris or aortic valve debris during the cutting procedure. FIG. 2, for instance, illustrates the relationship of the first collapsible plate 50 with respect to the first elongated instrument 20, the second elongated instrument 30, and the second collapsible plate 40. Preferably, the first collapsible plate and the second collapsible plate are on opposite sides of the damaged heart valve to create a confined or a closed space. Thus, in this example, the damaged heart valve is inside the confined space created by the first collapsible plate and the second collapsible plate. As a result, any debris and/or the damaged heart valve, when detached from the artery, are trapped between the first collapsible plate and the second collapsible plate.

In one example, the first collapsible plate may be self-expandable. Preferably, the diameter and the surface area of the first collapsible plate can be adjusted by advancement or withdrawal of an armature. Preferably, the advancement of an armature uncollapses/expands the first collapsible plate which can prevent escape of aortic valve debris. One end of the armature can be connected to the first collapsible plate, and preferably to the first collapsible plate and a non-mechanical cutting device and the other end of the armature can be outside of the patient to be used by the surgeon to advance or withdraw the armature. However, other methods known to one skilled in the art can also be used to expand the first collapsible plate.

The first collapsible plate can have similar characteristics and properties as the second collapsible plate. For example, the first collapsible plate can include pores/membrane/filter, marker(s) and/or optional stabilizers as previously described. Additionally, the first collapsible plate can also be made from the same material as the second collapsible plate. The first collapsible plate can be made from an opaque material or include a sensor to detect transmural penetration of an energy having a predetermined wavelength. One example of such energy is light energy, and more specifically a laser.

The non-mechanical cutting device can be any device that does not use a physical cutting surface to cut a tissue. The non-mechanical cutting device can be a light-generating cutting device (e.g., light energy cutting device) or a heat-generating cutting device. Preferably, the non-mechanical cutting device is an instrument that is capable of cutting through a tissue using energized particles, for example, a laser. Electrical energy could alternatively or in addition be used, for example, a cautery. Preferably, the non-mechanical cutting device is a laser capable of creating a cut through a calcified and/or fibrotic aortic valve of variable thickness, including normal living tissue. An example of such a laser is an excimer or holmium:YAG, which can be delivered through a flexible, or semi-flexible fiber. U.S. Pat. Nos. 5,688,261 and 5,722,970 illustrate the use of lasers, such as holmium:YAG laser, for surgery, and are incorporated in their entirety by reference herein. The excimer laser and holmium:YAG laser are commercially available through various companies such as LISA laser products in Germany. The flexible or semi-flexible fiber preferably can protrude through small transmural vascular apertures, such as the femoral artery or aortic wall. Preferably, the non-mechanical cutting device is capable of moving around the rotational axle device to make a substantially round annulus. In one example, the laser light is adapted to form the shape and size of the periphery of the diseased heart valve, thereby creating multiple cutting regions, which can substantially eliminate the need for moving the laser around the rotational axle device. Whether the laser is configured to have only one cutting region or multiple cutting regions, the rotational radius of the laser in relationship to the central axis of the second elongated instrument is preferably increased to approximately equal the outer diameter of the heart valve, as represented by laser 60 in FIG. 3. The increase in radius can be accomplished by advancing armature 65 connected to laser 60 and which passes through second elongated instrument 30 to be manually controlled by the operator from a position outside of the patient's body. The laser 60 can be rotated around the central axis by, for example, rotating the second elongated instrument to which the laser is attached through the armature 65.

Figure 3:
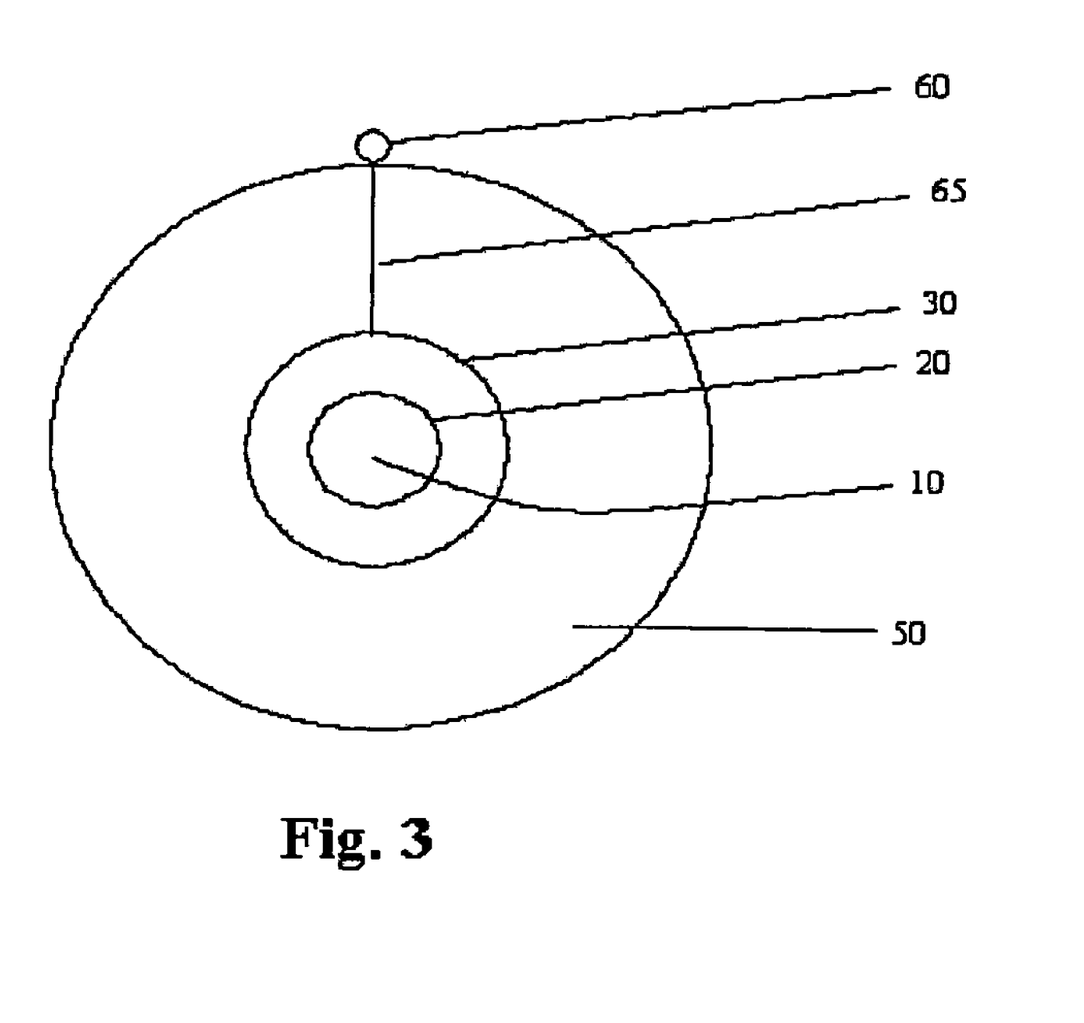
FIG. 3 is a sectional side view of FIG. 1, which includes a first collapsible plate, a non-mechanical cutting device, a guide device, a first elongated instrument, and a second elongated instrument.

FIG. 3 is an exemplary cross-section of the apparatus of the present invention. In FIG. 3, the first elongated instrument 20 is advanced over the guide device 10 and the second elongated instrument 30 is advanced over the first elongated instrument 20. Moreover, in FIG. 3, the first collapsible plate 50 can expand from the second elongated instrument 30 to the non-mechanical cutting device 60, which can be displaced radially from the second elongated instrument 30 by the armature 65.

In one example, wherein an off-pump percutaneous valve replacement technique is used, a device, preferably an inflatable balloon, capable of protecting the heart ventricle from blood reflux or from retrograde flow is preferably placed in the ascending aorta proximal to the valve plate. Once the cut valve passes over the balloon, the balloon can be inflated and then deflated. The inflation and deflation of the balloon can be controlled by an appropriate trigger, such as an electrocardiodiagram. Alternatively, if cardiac pumping activity is halted, the balloon can be inflated to protect the ventricle from the retrograde flow from an external pump source.

The present invention further relates to a method of cutting a tissue (e.g., a living tissue) using the apparatus described above. Preferably, as described previously, the tissue is a heart valve. A method of cutting the heart valve involves inserting the guide wire into a vascular system of a patient, navigating the guide device to a predetermined location and advancing the first elongated instrument over the guide device and navigating the first elongated instrument to a predetermined location. Preferably, the first elongated instrument is navigated through the heart valve and approximate to the heart valve. Moreover, the method includes advancing the second elongated instrument over the first elongated instrument and navigating the second elongated instrument to a predetermined location. Preferably, the second elongated instrument is navigated to the artery and approximate to the heart valve. The method also includes advancing the non-mechanical cutting device over the second elongated instrument to a predetermined location. Preferably, the non-mechanical cutting device is navigated to the artery and is also approximate to the heart valve. More preferably, the non-mechanical cutting device is movably connected to the second elongated instrument and is advanced to the artery with the second elongated instrument. The method further provides for the distal end of the first elongated instrument or the second elongated instrument having the first collapsible plate to be on one side of the heart valve and extending the first elongated instrument or the second elongated instrument having the second collapsible plate through the heart valve so that the distal end of the first elongated instrument or the second elongated instrument having the second collapsible plate is on opposing sides of the heart valve. Most preferably, the first elongated instrument, the second elongated instrument, the first collapsible plate, the second collapsible plate, and the non-mechanical cutting device are arranged outside of a patient's body and are advanced to the artery or heart as one system.

In one example, the guide device can be inserted into a vascular system of a patient through a peripheral artery. Preferably, the guide device is inserted into the femoral artery. The guide device is adapted to advance into the aorta and, preferably, into the heart past the damaged valve. A first elongated instrument can then advance over the guide device into the heart past the damaged heart valve. Preferably, a second collapsible plate is adapted to advance through the first elongated instrument into the heart past the damaged valve. More preferably, the first elongated instrument and the second collapsible plate are arranged outside of a patient's body and can be advanced to the heart as one system. The first elongated instrument having the second collapsible plate can be advanced over the guide device into the heart and past the damaged valve. Once the first elongated instrument having the second collapsible plate is placed past the damaged valve, the second collapsible plate can be expanded. Preferably, the uncollapsed (expanded) form of the second collapsible plate is proximate to the damaged heart valve.

Figures 4A, 4B:
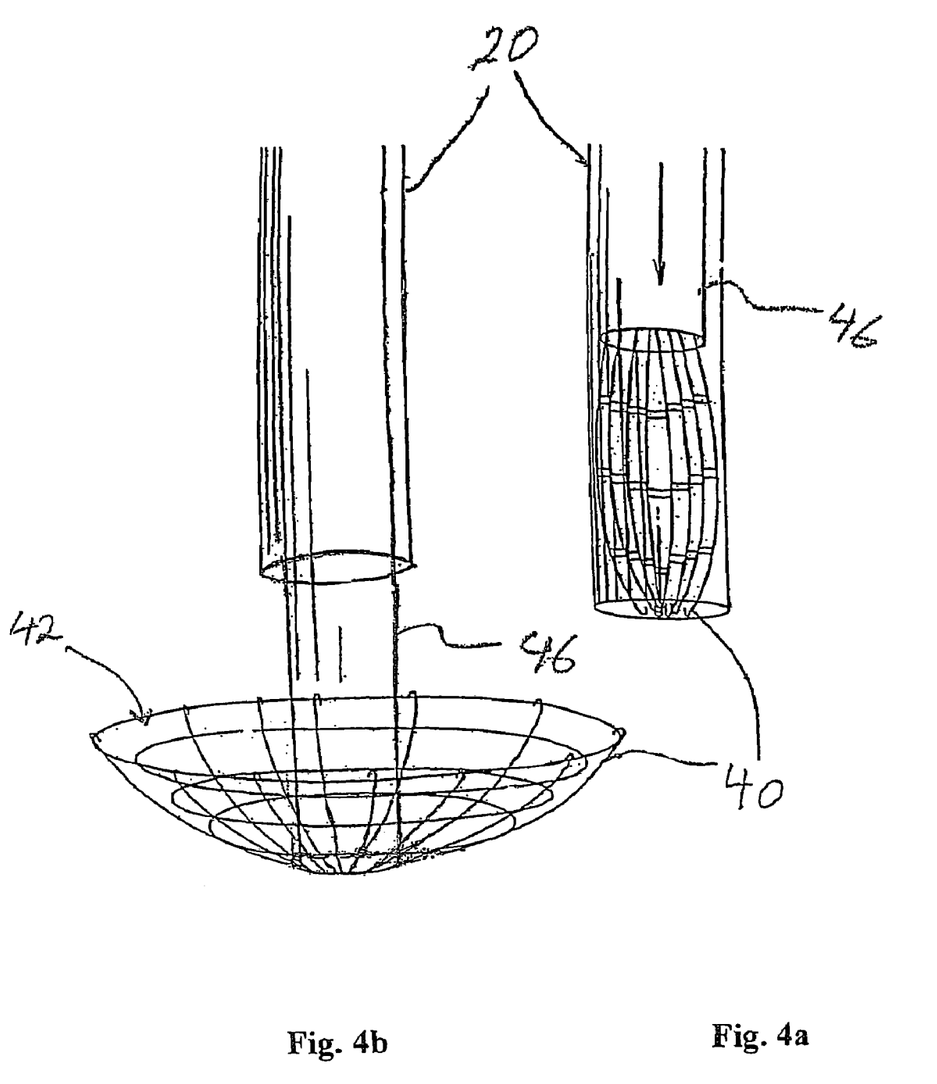
FIGS. 4(a) and 4(b) are schematic diagrams of the second collapsible plate having a retractable cone-shaped end.
Figure 5:
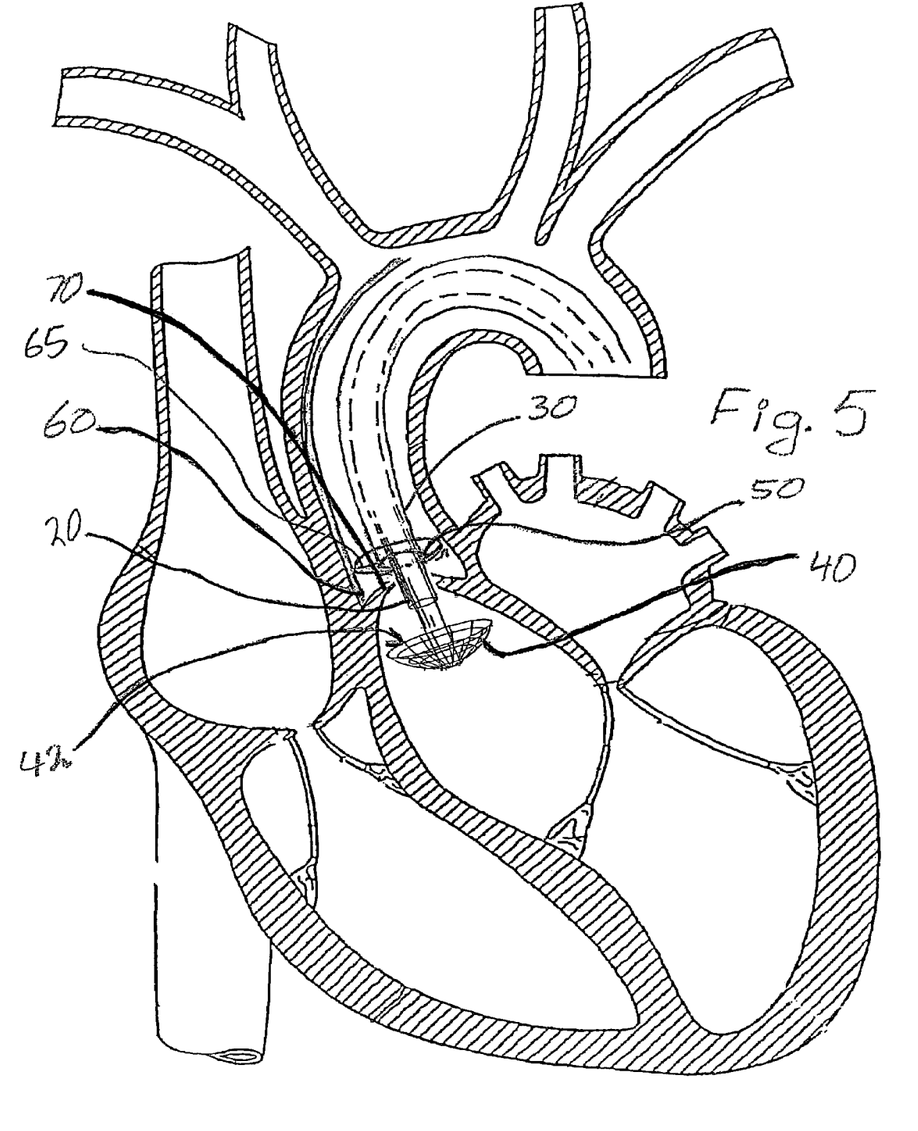
FIG. 5 is a schematic diagram of the heart, the aortic valve, the first collapsible plate, the non-mechanical cutting device that is connected to the armature, the guide device, the first elongated instrument, the second elongated instrument, and the second collapsible plate of the present invention.
Figure 6:
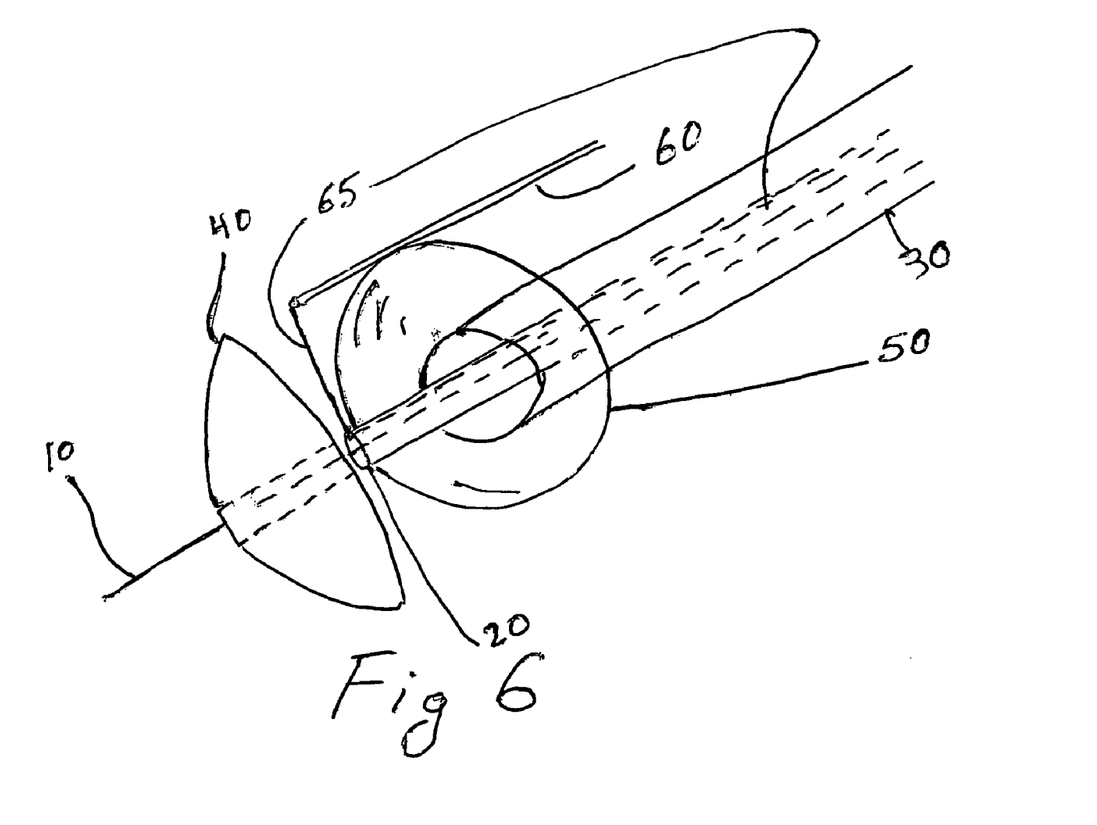

In one example, as illustrated in FIGS. 4(a) and 4(b), the second collapsible plate is capable of forming a cone with its open face (area opposite to the tip of the core), facing a damaged heart valve. FIG. 5 is an exemplary configuration of the second collapsible plate 40 with its open face 42 facing the damaged heart valve 70. The second collapsible plate 40, shown at FIG. 4(a), can protrude out as shown at FIG. 4(b) from the distal end of the first elongated instrument 20 to create a large surface area (open face 42). Preferably, struts or parachute cords are used to protrude and expand the second collapsible plate 40. For example, when using a strut, while keeping the first elongated instrument fixed in a position, the strut can push the second collapsible plate out of the first elongated instrument, thereby uncollapsing (e.g., opening) the second collapsible plate. As shown in FIG. 4(b), the strut 46 pushes second collapsible plate 40 while keeping the first elongated instrument 20 fixed in a position to expand or uncollapse the second collapsible plate 40. FIG. 5 shows the second collapsible plate 40 (in an opened fashion) substantially covering the damaged valve 70.

Preferably, the second elongated instrument is adapted to advance over the first elongated instrument to a predetermined location. Preferably, the second elongated instrument is adapted to advance to the area of the heart having the damaged valve. More preferably, the second elongated instrument is placed in the artery approximate to the damaged valve. Most preferably, the first elongated instrument is on one side of the damaged valve and the second elongated instrument is on the opposing side of the damaged valve. Most preferably, the first elongated instrument is passed through the heart valve approximate to the damaged valve and the second elongated instrument is located in the artery on the opposing side and approximate to the damaged heart valve.

The first collapsible plate can be advanced approximate to the damaged valve over the second elongated instrument. Preferably, the first collapsible plate is initially connected to the second elongated instrument and the second elongated instrument having the first collapsible plate is advanced over the first elongated instrument to a predetermined location approximate to the damaged tissue or valve. Preferably, the distal end of an armature is connected to the first collapsible plate and the proximal end of the armature is outside of the patient. Preferably, the armature is advanced and connected to the first collapsible plate through the first elongated instrument or the second elongated instrument. Once the first collapsible plate is placed approximate to the damaged tissue or valve, the first collapsible plate can be expanded, by advancing the armature, to have a surface area that substantially covers an area from the surface of the second elongated instrument to the non-mechanical cutting device. Preferably, the first collapsible plate is expanded by advancement of an armature. In one example, the armature can also be connected to the non-mechanical cutting device and can extend between the second elongated instrument and the non-mechanical cutting device. The first collapsible plate can expand to circular sizes of different radiuses depending on the extent to which the armature is advanced. The ability of the first collapsible plate to expand can be a function of the intrinsic shape properties of the plate, or it can be related to a circular rim which is expandable and which can be attached to the non-mechanical cutting device and/or to the armature.

The non-mechanical cutting device can movably be connected to the first elongated instrument by an armature or can movably be connected to the second elongated instrument by the armature. Preferably, the non-mechanical cutting device is connected to the first collapsible plate. In one example, in which the non-mechanical cutting device is connected to the first collapsible plate, the non-mechanical cutting device is adapted to advance with the first collapsible plate over the second elongated instrument. More preferably, the second collapsible plate 40, the first elongated instrument 20, the second elongated instrument 30, the first collapsible plate 50, the armature 65, and the non-mechanical cutting device 60 are arranged outside of a patient's vascular system and then this arrangement is advanced into the patient's vascular system to a predetermine location as shown in FIG. 5.

Preferably, the non-mechanical cutting device is radially displaced from the rotational axle device. The length of displacement can be varied based upon the internal diameter of the aortic valve. Preferably, the non-mechanical cutting device is set several millimeters shorter than the aortic annulus. The non-mechanical cutting device can be introduced and withdrawn in a "closed" position (i.e., minimal radial displacement), and can be set to the desired diameter by advancing an armature from within the rotational axle device. Preferably, the non-mechanical cutting device includes at least one marker for determining its position within the cardiovascular system of a patient.

Preferably, when the first collapsible plate and the second collapsible plate are expanded, they form a confined or closed area. Preferably, the damaged tissue or damaged heart valve is located in this confined area between the first collapsible plate and the second collapsible plate. Preferably, the surface area of the first collapsible plate, when in an uncollapsed form, covers an area from the surface of the second elongated instrument to the non-mechanical cutting device. Preferably, the open face of the second collapsible plate covers the entire area of the damaged tissue or damaged heart valve. Preferably, the non-mechanical cutting device is adapted to cut the circumference of the valve or tissue at the area in which the valve or tissue is connected to the vessel/artery without cutting or damaging any portion of the vessel/artery. The non-mechanical cutting device cuts the circumference of the valve or tissue by rotating the non-mechanical cutting device along the rotational axle device. Preferably, the non-mechanical cutting device is rotated 360° around the rotational axle device until a fully circumferential cut of the damaged valve is achieved.

In one example, in which more than one non-mechanical cutting device is used, a need may not exist to rotate all or any of the non-mechanical cutting devices 360° around the rotational axle device to fully cut out the aortic valve. When multiple non-mechanical cutting devices are used, preferably each non-mechanical cutting device is placed at a predetermined location substantially the same distance away from the rotational axle device. More preferably, each non-mechanical cutting device forms the same angle with respect to its adjacent non-mechanical cutting device. For example, if only two non-mechanical cutting devices are used, the angle between the two non-mechanical cutting devices is 180°. When four non-mechanical cutting devices are used, the angle between the four non-mechanical cutting devices is 90°. In this example, the first non-mechanical cutting device can be rotated around the rotational axle device for a distance to reach the starting point of the second non-mechanical cutting device. In this example, the second non-mechanical cutting device can be rotated around the rotational axle device for a distance to reach a third non-mechanical cutting device (if available) and so forth. When a third non-mechanical cutting device is not used, the second non-mechanical cutting device can be rotated around the rotational axle device for a distance to reach the starting point of the first non-mechanical cutting device, thereby making a full circumferential cut of the damaged valve. In one example, the laser light can be adapted or diffused or diffracted to form the shape (e.g., oval-shaped or ring-shaped) of the periphery of the heart valve. Depending on the number of cutting regions, there may not be a need to rotate the laser around the rotational axle device.

Once the damaged tissue or the damaged heart valve has been cut, the freed damaged tissue can be obtained and trapped between the expanded first collapsible plate and the expanded second collapsible plate and can be extracted from the vascular system of a patient by removing the first expanded collapsible plate and the second expanded collapsible plate from the peripheral artery. The first collapsible plate and the second collapsible plate may need to be partially or fully compressed or diminished in diameter. Preferably, the first collapsible plate and the second collapsible plate can be compressed by the cords or struts attached to the collapsible plates, or by external compression of the femoral artery to facilitate extraction from the peripheral artery. In one example, to prevent reflux of blood back into the ventricle before inserting a new artificial valve, an optional balloon at distal end of the guide device can be inflated. The new artificial valve can then be inserted percutaneously over the guide device and be positioned accordingly.

Preferably, the percutaneous valve procedure is performed without the use of cardiopulmonary bypass. It is preferable to incorporate a temporary valve mechanism into the apparatus for cutting and removing tissue (valve extraction mechanisms) to protect the heart ventricle from reflux of blood from the aorta during the period between the native valve excision and permanent prosthetic valve implantation.

Alternatively, in case of cardiovascular dysfunction or for other indications, the percutaneous valve should be removed during percutaneous bypass. When the percutaneous valve is removed during percutaneous bypass, cardiac left ventricle needs to be protected from retrograde flow of blood during the period from excision of the native valve to implantation of the permanent prosthetic valve. The retrograde blood flow is usually from the extracorporeal circuit, which flows through the aorta and into the unprotected ventricle.

In case of off-pump percutaneous valve replacement, an inflatable balloon can be incorporated onto the rotational axle device or a coaxially internal component. The inflatable balloon is preferably situated in the aorta proximal to the valve plates. The balloon can be collapsed during extraction of the valve, wherein the valve extraction mechanisms advance or regress over the rotational axle and/or guide wire. During extraction, once the valve/valve mechanism passes over the balloon, preferably after the native valve is partially or completely excised, the balloon can be inflated and then deflated by an appropriate trigger, such as an electrocardiogram. The inflation and deflation of the balloon, which is preferably timed, functions as a temporary valve, which protects the ventricle from reflux during diastole. The balloon can be temporarily deflated as the percutaneous valve passes over the guide wire/rotational axle, and then re-activated to protect the ventricle, as needed, until the percutaneous valve is utilized.

In the case of the off-pump apparatus wherein, preferably, the balloon is alternatingly deflated immediately prior to systole (ventricular contraction) and inflated at the start of diastole (ventricular relaxation), it is important to differentiate the deflation and inflation of the balloon from the pumping action of a standard intra-aortic balloon pump (IABP). In the latter, a balloon having a volume of about 30-40 $cm^3$ serves to displace sufficient blood volume in an antegrade and retrograde fashion to create a blood pumping mechanism. Such a mechanism would be disadvantageous to use in the present invention because, in the absence of an aortic valve, such volume displacement would create a significant blood reflux into the ventricle. Preferably, a retrograde pumping action with the present invention is avoided by: 1) minimizing the volume of the balloon, 2) positioning the balloon in the ascending aorta (as opposed to the placement of the IABP in the descending aorta) to minimize the amount of blood located proximal to the balloon, which can create a retrograde displacement, and 3) configuring the balloon into a "disc-like" shape, to occlude the aorta while minimizing its fluid displacement volume.

Alternatively, if a bypass surgery is performed and cardiac pumping activity is halted (i.e., minimal blood is ejected from the ventricle), the balloon can be stably inflated to protect the ventricle from retrograde flow from an external pump source. Any forward ejection of blood from the ventricle will naturally be routed down the coronary arteries. Additionally, a small bypass channel can be incorporated into the rotational axle, or through the balloon, to provide supplemental blood to the coronary ostia, if needed.

The temporary valve can optionally then be replaced with a permanent valve. Any conventional heart valve prosthesis and procedure can be utilized to replace the temporary valve with a permanent valve, as described, for example, in U.S. Pat. Nos. 5,480,424; 5,352,240; 5,984,959; 6,203,553 B1; 6,309;417 B1; 6,413,274 B1, and 6,638,303 B1, each of which is incorporated in its entirety herein by reference.

Other embodiments of the present invention will be apparent to those skilled in the art from consideration of the present specification and practice of the present invention disclosed herein. For example, this device and methodology may be applied to the mitral or any of the other heart valves. Furthermore, this device may be used in the context of cardiopulmonary bypass, and may include the use of any number of percutaneous valve delivery devices, any number of techniques or methods of venting the heart, any number of methods for protecting the heart from aortic reflux with temporary valve devices, and/or arresting the heart with cardioplegic solutions or other techniques. It is intended that the present specification and examples be considered as exemplary only with a true scope and spirit of the invention being indicated by the following claims and equivalents thereof.

What is claimed is:

1. An apparatus for cutting and removing living tissue comprising:
    a rotational axle device;
    at least one non-mechanical cutting device adapted to be radially displaced from said rotational axle device upon deployment; and
    a first collapsible plate adapted to cover an area from said rotational axle device to said at least one non-mechanical cutting device,
    wherein said rotational axle device comprises a guide device; a first elongated instrument having a proximal end and a distal end; a second elongated instrument adapted to advance over said first elongated instrument and having a proximal end and a distal end; and a second collapsible plate, and
    wherein said non-mechanical cutting device is movably connected to said first elongated instrument or to said second elongated instrument,
    wherein said first collapsible plate or said second collapsible plate is associated with said first elongated instrument or said second elongated instrument.

2. The apparatus of claim 1, wherein said guide device comprises a hemostatic object.

3. The apparatus of claim 1, wherein said second collapsible plate is of a diameter sufficient to pass through a heart valve when in a collapsed position.

4. The apparatus of claim 1, wherein said second collapsible plate is from about 2 mm to about 10 mm in diameter when said second collapsible plate is in a collapsed form.

5. The apparatus of claim 1, wherein said second collapsible plate is from about 15 mm to about 25 mm in diameter when said second collapsible plate is in an expanded form.

6. The apparatus of claim 1, wherein said second collapsible plate comprises a filter which permits blood flow, and prevents any loose tissue from flowing in a vascular system of a patient.

7. The apparatus of claim 1, wherein said second collapsible plate is at said distal end of said first elongated instrument or said second elongated instrument.

8. The apparatus of claim 1, wherein said second collapsible plate is conical in shape.

9. The apparatus of claim 1, wherein said second collapsible plate is adapted to detect transmural penetration of an energy having a predetermined wavelength.

10. The apparatus of claim 1, wherein said first collapsible plate is adapted to cover an area extending from an outer surface of said first elongated instrument to inner surface of said second elongated instrument, wherein said second elongated instrument has a diameter about equal to an inner diameter of a vessel at a location wherein said tissue is connected to said vessel.

11. The apparatus of claim 1, wherein said first collapsible plate is adapted to cover an area extending from an outer surface of said first elongated instrument or outer surface of said second elongated instrument to said non-mechanical cutting device.

12. The apparatus of claim 1, wherein said first collapsible plate expands by advancement of an armature.

13. The apparatus of claim 1, wherein said first collapsible plate and said second collapsible plate are magnetized.

14. The apparatus of claim 1, wherein said non-mechanical cutting device is a light-generating cutting device or a heat-generating cutting device.

15. The apparatus of claim 14, wherein said light-generating cutting device is a laser.

16. The apparatus of claim 15, wherein said tissue having a periphery and said laser is adapted to generate a laser beam, wherein said laser beam is adapted, diffused or diffracted to form a shape substantially similar to periphery of said tissue.

17. The apparatus of claim 14, wherein said heat generating cutting device is a cauterizing device.

18. The apparatus of claim 1, wherein said non-mechanical cutting device is movably connected to said first elongated instrument or said second elongated instrument by an armature.

19. The apparatus of claim 1, wherein said rotational axle device includes a heart ventricle protecting device to protect said heart ventricle from reflux of blood, from retrograde blood flow, or combinations thereof.

20. The apparatus of claim 19, wherein said heart ventricle protecting device is an inflatable balloon.

21. The apparatus of claim 19, wherein said heart ventricle protecting device includes a disc configuration.

22. The apparatus of claim 19, wherein said heart ventricle protecting device is a temporary valve.

23. A method of cutting a heart valve using an apparatus for cutting and removing living tissue, said apparatus comprising:
    a rotational axle device;
    at least one non-mechanical cutting device radially displaced from said rotational axle device;
    a first collapsible plate adapted to cover an area from said rotational axle device to said at least one non-mechanical cutting device,
    wherein said rotational axle device comprises a guide device; a first elongated instrument having a proximal end and a distal end; a second elongated instrument adapted to advance over said first elongated instrument and having a proximal end and a distal end; and a second collapsible plate, wherein said method comprising:
    inserting said guide device into a vascular system of a patient;
    navigating said guide device to a pre-determined location;
    advancing said first elongated instrument, adapted to include said first collapsible plate or said second collapsible plate, over said guide device and navigating said first elongated instrument to a predetermined location;
    advancing said second elongated instrument, adapted to include said first collapsible plate or said second collapsible plate, over said first elongated instrument and navigating said second elongated instrument to a predetermined location; wherein a non-mechanical cutting device is part of said second elongated instrument or is separately advanced over said second elongated instrument to a predetermined location;
    extending said first elongated instrument or said second elongated instrument having said second collapsible plate through said heart valve, wherein said distal end of said first elongated instrument or said second elongated instrument having said second collapsible plate is on one side of said heart valve and said distal end of said first elongated instrument or said second elongated instrument having said first collapsible plate is on opposing sides of said heart valve;

expanding said first collapsible plate;

expanding said second collapsible plate; and cutting said heart valve by said non-mechanical cutting device.

24. The method of claim 23, wherein said non-mechanical cutting device is movably connected to said first elongated instrument or said second elongated instrument.

25. The method of claim 23, further comprising extracting said non-mechanical cutting device from said vascular system of said patient; and extracting said first collapsible plate and said second collapsible plate from said vascular system of said patient, including said heart valve located between said first and second collapsible plates.

26. The method of claim 23, wherein said first elongated instrument, said second elongated instrument, said first collapsible plate, said second collapsible plate, and said non-mechanical device are first arranged outside of said patient prior to said inserting.

27. The method of claim 23, wherein said apparatus includes a heart ventricle protecting device and further comprising advancing said heart ventricle protecting device over said rotational axle device or said guide wire.

28. The method of claim 23, wherein said apparatus includes a heart ventricle protecting device and further comprising advancing said heart ventricle protecting device to aorta proximal to a valve plate.

29. The method of claim 23, wherein said apparatus includes a heart ventricle protecting device that is adapted to be inflated and further comprising inflating said heart ventricle protecting device after said cut heart valve is passed over said heart ventricle protecting device.

30. The method of claim 29, wherein said cut heart valve is at least partially excised prior to inflating said heart ventricle protecting device.

31. The method of claim 23, wherein said apparatus includes a heart ventricle protecting device and wherein said heart ventricle protecting device is inflated and deflated by a trigger mechanism.

32. The method of claim 31, wherein said trigger mechanism is an electrocardiogram.

33. A method for cutting a heart valve comprising:

positioning a first collapsible plate in an artery approximate to said heart valve;

positioning a second collapsible plate in a heart chamber approximate to said heart valve;

positioning at least one non-mechanical cutting device approximate to said heart valve;

cutting said heart valve;

removing said heart valve;

expanding a hemostatic object at distal end of a guide device; and inserting a new heart valve.

* * * * *